United States Patent [19]

Smith

[11] 4,440,184
[45] Apr. 3, 1984

[54] DENTAL FLOSSING DEVICE

[76] Inventor: Eric L. Smith, 638 Potomac Ave., Hagerstown, Md. 21740

[21] Appl. No.: 392,136

[22] Filed: Jun. 25, 1982

[51] Int. Cl.³ .............................................. A61C 15/00
[52] U.S. Cl. ........................................................ 132/91
[58] Field of Search .................................... 132/91–93; D28/64

[56] References Cited

U.S. PATENT DOCUMENTS

| D. 251,075 | 2/1979 | Schiff ................................... D28/64 |
| 2,828,754 | 4/1958 | Stewart ................................. 132/91 |
| 3,236,247 | 2/1966 | Brockman .............................. 132/91 |
| 3,387,615 | 6/1968 | MacKew ................................ 132/91 |
| 3,472,247 | 10/1969 | Borsum et al. ....................... 132/91 |
| 3,474,799 | 10/1969 | Cappello .............................. 132/91 |
| 3,918,466 | 11/1975 | Peebles ................................ 132/91 |
| 4,002,183 | 1/1977 | Restall ................................. 132/91 |
| 4,006,750 | 2/1977 | Chodorow ............................. 132/91 |
| 4,304,246 | 12/1981 | Yafai .................................. 132/96 |

FOREIGN PATENT DOCUMENTS 450928  7/1936  United Kingdom ............. 132/92 R

*Primary Examiner*—C. Fred Rosenbaum
*Assistant Examiner*—Sherri E. Vinyard
*Attorney, Agent, or Firm*—James L. Bean

[57] ABSTRACT

An improved dental flossing device includes an elongated handle supporting at one end a generally star-shaped floss holding head including a plurality of generally radially extending fingers disposed in a common plane extending transversely of the handle. A floss positioning groove is formed in the distal end of each finger for receiving and retaining a closed loop of dental floss whereby a plurality of sections of the floss loop are presented one between each adjacent pair of fingers for flossing the teeth. After use, the loop of floss can be easily removed and a new loop installed.

10 Claims, 8 Drawing Figures

DENTAL FLOSSING DEVICE

BACKGROUND OF THE INVENTION

1. Field of the Invention

This invention relates to dental flossing devices, and more particularly to an improved dental flossing device employing closed loops of floss supported to efficiently and effectively floss the teeth.

2. Description of the Prior Art

The benefits of regular use of dental floss have long been recognized and continue to be stressed by the dental profession as a vital part of a comprehensive dental care program. However, many people find it inconvenient or difficult to use dental floss at least partially because of difficulty in maneuvering the floss betwween the back teeth with the fingers. Indeed, this difficulty of maneuvering dental floss with the hands, coupled with the difficulty in forcing the floss between teeth which are very close together, makes it virtually impossible for some people to properly floss in this manner. Accordingly, a number of flossing devices have been developed in an attempt to facilitate holding the floss under the proper tension and at the desired orientation for use. The most popular of these prior art flossing devices generally have had a pair of spaced arms across which a length of dental floss is strung and either secured at the ends as by wrapping or wedging into a narrow slot, or by holding the free end with the hands. A supply of dental floss is provided, as on the handle, of certain of these prior art devices whereas in others it is necessary to sever the desired length of floss from a conventional supply spool and then secure it to the holder. In either case, properly securing the floss to the holder is a tedious task and proper tensioning for effective flossing is not always achieved.

Flossers of the so-called disposable type are also known in which a length of floss is permanently secured in position for use, examples of such devices being found in U.S. Pat. Nos. 3,918,466 and 4,006,750. While such devices eliminate the problem of manually installing the floss, they are nevertheless relatively expensive, particularly when it is considered that the single length of floss conventionally employed frequently becomes frayed or even breaks before the user can floss all of his teeth, thereby making it necessary to use more than one of the devices for a single flossing. Further, the floss generally has not been held in the most convenient position for use.

U.S. Pat. No. 4,304,246 discloses a dental floss holder in the form of a resilient strip bent and retained in a generally U-shaped configuration over which an endless band of dental floss is positioned, with the resiliency in the holder arms applying the necessary tension to the floss. This device, however, is not easily maneuvered in the back portion of the mouth and holding the device frequently results in the arms being resiliently pressed toward one another thereby lessening the tension in the floss.

It is the object of the present invention to provide an improved dental flossing device which is easy and convenient to use and which avoids the shortcomings of the prior art devices as briefly outlined above.

More particularly, it is an object of the present invention to provide an improved dental flossing device including an elongated handle having at one end a floss support head presenting a plurality of fingers for supporting a closed loop of dental floss in a position in which it is more easily and efficiently used for flossing all of the teeth in the user's mouth.

Another object is to provide such a dental flossing device wherein the floss supporting head is generally in the configuration of a star wheel, including a plurality of radial fingers disposed in a common plane and extending transversely of an elongated handle and wherein dental floss supported on the elongated fingers presents a plurality of tensioned segments for use in flossing the teeth.

Another object is to provide such a dental flossing device wherein an endless loop of dental floss is positioned around and supported by the end portions of a plurality of radially extending fingers whereby the portion of floss extending between each adjacent pair of such fingers may be used in flossing the teeth.

Another object is to provide such a dental flossing device wherein an endless loop of dental floss is elastically stretched onto and supported by a plurality of substantially rigid radially extending fingers and wherein the dental floss has sufficient elastic resilience to maintain desired tension for flossing the teeth when installed.

Another object is to provide such a flossing device which may be used to simultaneously floss both upper and lower teeth.

Another object is to provide such a flossing device wherein bite pressure may be used to facilitate inserting the floss between the teeth.

Another object is to provide such a dental flossing device which is inexpensive to manufacture and on which the endless loop of dental floss may be easily installed and removed for maximum convenience in use.

BRIEF DESCRIPTION OF THE DRAWINGS

The foregoing and other objects and advantages of the invention will be apparent from the detailed description contained hereinbelow, taken in conjunction with the drawings, in which.

DESCRIPTION OF THE PREFERRED EMBODIMENT

Figure 2:
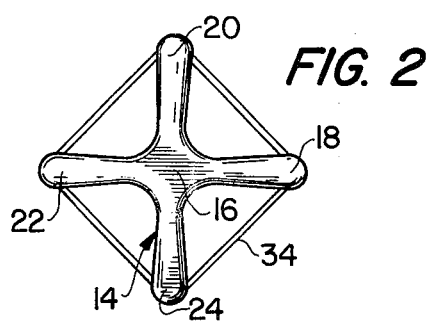
FIG. 2 is an end elevation view of the flossing head portion of the dental flossing device shown in FIG. 1.
Figure 1:
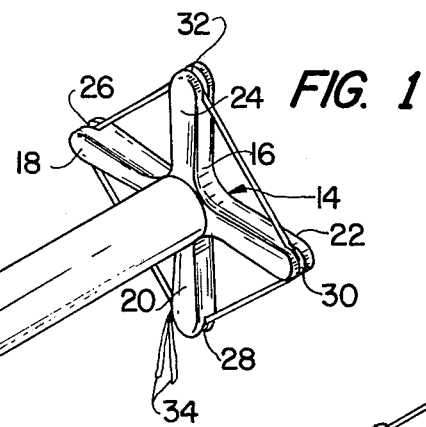
FIG. 1 is an isometric view of the improved dental flossing device according to the present invention.
Figure 3:
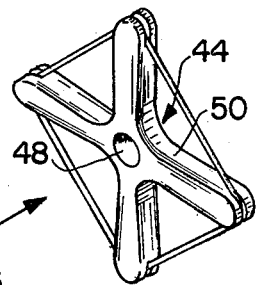
FIG. 3 is a fragmentary exploded view illustrating an alternate embodiment of the invention.
Figure 4:
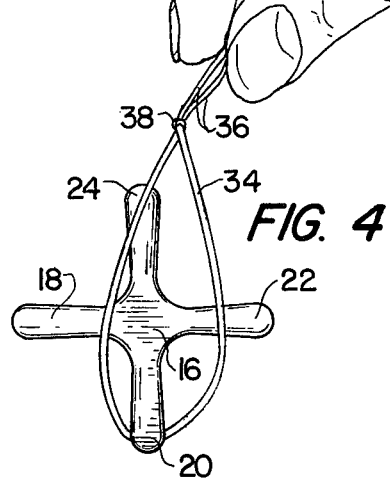
FIG. 4 is a view similar to FIG. 2 and illustrating a closed loop of floss being manually installed on the flossing device.

Referring now to the drawings in detail, the improved dental flossing device of the present invention is designated generally by the reference numeral 10 and includes an elongated handle 12 supporting at one end a floss supporting head 14 in the form of a central hub 16 having a plurality of radially extending fingers 18, 20, 22, and 24 integrally formed thereon at equally spaced intervals therearound. Fingers 18, 20, 22 and 24, respectively, each has a shallow notch, or groove 26, 28, 30, 32 respectively in its distal end as seen in FIGS. 1 and 3. In practice, the grooves in the ends of the fingers are relatively shallow, being only deep enough to engage and reain a length of dental floss in position, although in FIGS. 1 and 3 these grooves are shown somewhat exaggerated in depth for clarity. Handle 12 and floss support head 14 may be integrally molded from a unitary mass of synthetic resin material.

A closed loop 34 of dental floss may be mounted on the floss supporting head 14 with the floss extending under desirable tension between the end portions of each pair of adjacent fingers around the head to present four separate segments of floss in position for use in flossing the teeth.

As is known, most dental floss sold commercially is manufactured from nylon or polyester material and comprises a single substantially untwisted strand made up of a plurality of individual filaments. The strand may be either waxed or unwaxed. Such individual strands may be elongated substantially under tension and have the ability for elastic recovery after being elongated up to 15%, or more, depending on strand size and manufacturer's specification. This ability of elastic recovery after substantial elongation makes it possible to form the floss into a closed loop which may be mounted within the grooves 26, 28, 30 and 32, with the closed loop being dimensioned so that it must be elastically stretched in order to be forced into the final groove around the star wheel shaped floss support head. Once manually stretched over the nonyielding floss support head, the floss loop will provide a constant fixed maximum desirable tension but will yield slightly under further stress and thus can easily be forced into the interstices between adjacent teeth to provide effective flossing.

Figure 5:
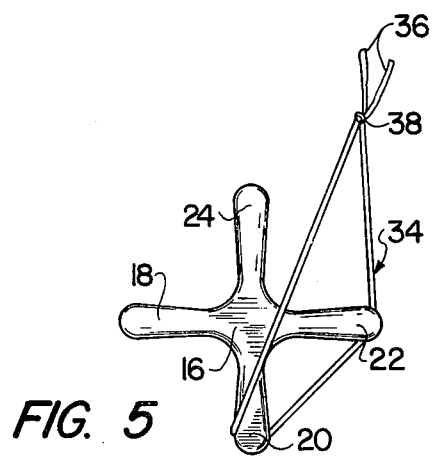
FIGS. 5-7 are views similar to FIG. 4 and illustrating progressive steps in installing the endless loop of dental floss.
Figure 6:
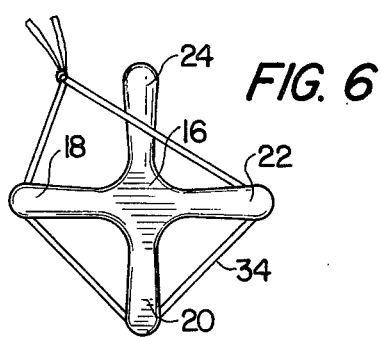
Figure 7:
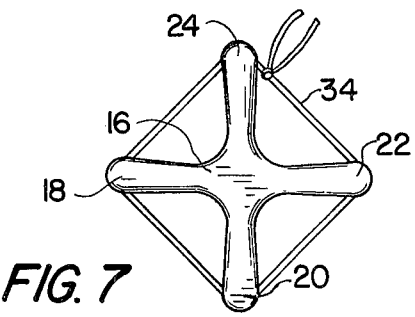

Commercial grades of dental floss may be tied into accurately dimensioned closed loops either by use of a knotting machine or manually with the knots being drawn sufficiently tight so that they will not slip under the normal tensile loads used in flossing the teeth. In this regard, however, the unwaxed floss is desirable both from the standpoint of operating of the knotting apparatus and because there is less tendency for a knot in the unwaxed floss to slip under tensile loads during use. The knotted loop is preferably severed from the floss supply leaving a short length, for example 1 to 2 inches, of floss as free ends or tails 36 extending from the knot 38. The tails 36 provide a convenient means for manually installing a closed loop of floss onto the substantially rigid fingers of the flossing head 14. As illustrated in FIGS. 4–7, the tails 36 can be gripped between the thumb and forefinger of one hand and the closed loop positioned within the groove in the free end of one of the fingers as the flossing device is held in the other hand. The endless loop may then be manipulated to be positioned into the endless groove of the other fingers progressively around the flossing head as schematically illustrated in FIGS. 5–7, with finger pressure being applied to the tails 36 to stretch the floss sufficiently to snap it into the floss retaining groove in the final finger. This tends to locate the knot 38 at or near the distal end of one of the fingers, i.e., the last finger into which the closed loop 34 of floss is positioned, so that the loop then is presented in four substantially equal unobstructed segments for use in flossing the teeth. Thus, the multiple lengths of exposed floss allows extended use of the instrument without reflossing. However, when reflossing is desired, it is only necessary to pull slightly on the tails 36 to remove the loop from the floss retaining groove in one finger and the used floss loop is then easily removed for disposal.

Since the usable lengths of floss are all disposed in a plane extending substantially perpendicular to the handle, the floss is easily manipulated into position for use. The angle of the particular length of floss being used generally corresponds to the plane of the interproximal tooth surfaces to be cleaned so that maximum efficiency is achieved. Also, the angular position of the handle relative to the star wheel shaped floss holding head enables bite pressure to be applied to force the floss into the interstices between tight teeth. The arrangement of the respective lengths of floss is such that both upper and lower teeth may readily be flossed at the same time.

By utilizing the natural elastic resilience of the nylon filaments of the dental floss to retain it on the flossing head and to provide the desired tension, the correct tension for proper flossing can always be assured. Proper tension on the floss allows ease of entry between the teeth and prolongs floss life by reducing fraying or tearing of the filaments. Since proper tension is maintained automatically by the present invention, all manual effort may be directed to proper manipulation of the device to place the floss between the teeth and in manipulating the floss to remove plaque and food particles from the interproximate surfaces.

A further advantage of the present invention is that, where increased thickness of floss is required or where less resilient deflection is desired, multiple floss loops may easily be positioned onto the holder.

Figure 8:
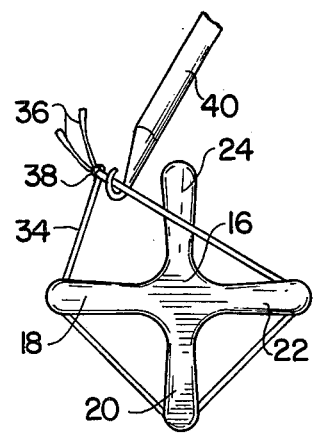
FIG. 8 is a view similar to FIG. 6 and illustrating an alternate means for installing the floss on the floss head.

For persons lacking the necessary manual dexterity to position a loop of floss on the flossing head in the manner illustrated in FIGS. 4-7, because of some infirmity or the like, a small hook shaped instrument 40 may be provided to apply the necessary tension to place the loop on the head in the manner illustrated in FIG. 8.

In an alternate embodiment of the invention illustrated in FIG. 3, the handle 42 and flossing head 44 are manufactured as separate elements which may be easily assembled and frictionally retained together. In this embodiment, handle 42 is provided with a tapered, or generally cone-shaped end portion 46 adapted to be telescopingly received in a correspondingly tapered complimentary opening 48 in the central hub portion of the star wheel shaped floss head 44. Friction contact between the two cone-shaped surfaces firmly holds the floss head on the handle.

While preferred embodiments of the invention have been disclosed and described in detail, it should be understood that the invention is not so limited but rather that it is intended to include all embodiments thereof which would be apparent to one skilled in the art and which come within the spirit and scope of the invention.

What is claimed is:

1. A dental flossing instrument comprising an elongated handle,
    a generally star wheel shaped floss support head on one end of the handle,
    said floss support head including a central hub portion and more than two support fingers extending generally radially from said central hub portion and from said handle and being located in substantially equally spaced relation to one another around said hub portion, and
    an endless loop of dental floss releasably supported on said support fingers in a plane disposed substantially perpendicular to said handle,
    said fingers each terminating in a free end having a floss retaining groove therein for receiving and releasably retaining said endless loop of dental floss stretched around the support head whereby a portion of said dental floss loop extends between said free end portions of each adjacent pair of fingers around said hub portion and in laterally spaced relation to said handle to thereby provide more than two of said floss loop portions each supported in position for flossing the teeth.

2. The dental flossing instrument according to claim 1 wherein said handle and said floss support head are integrally molded from a unitary substantially homogenous mass of synthetic resin material.

3. The dental flossing instrument according to claim 2 wherein said floss support head comprises four of said fingers and wherein said closed loop of dental floss is supported in two pairs of spaced parallel lengths with the lengths of floss of the two pairs being substantially perpendicular to one another.

4. The dental flossing instrument according to claim 2 wherein said handle and said floss support head are formed as separate units and wherein said floss support head is releasably mounted on said one end of said handle.

5. A dental flossing instrument comprising, in combination,
an elongated handle,
a generally star wheel shaped floss support head on one end of the handle
said floss support head including a central hub portion and more than two support fingers extending generally radially from said central hub portion and from said handle and being located in substantially equally spaced relation to one another around said hub portion, said fingers each terminating in a free end having a floss retaining groove therein, said floss retaining grooves being disposed in a common plane extending substantially perpendicular to said elongated handle, and a closed loop of dental floss extending around the support head and engaging each said finger within said groove formed in the end thereof, the length of the dental floss in said closed loop in an unstressed condition being slightly less than the distance around said floss support head whereby the closed loop is elastically extended when installed on the floss support head and whereby the portion of the closed loop extending between each adjacent pair of said fingers is supported in position for use in flossing the teeth and is maintained under tension to facilitate such use.

6. The dental flossing instrument according to claim 5 wherein said closed loop of dental floss comprises a length of floss formed into a closed loop by a knot.

7. The dental flossing instrument according to claim 6 wherein said closed loop of dental floss further comprises at least one free end portion of floss extending from the knot, the free end portion having a length sufficient to be grasped with the hand to install the closed loop on the floss support head.

8. The dental flossing instrument according to claim 7 wherein said handle and said floss support head are integrally molded from a unitary substantially homogenous mass of synthetic resin material.

9. The dental flossing instrument according to claim 8 wherein said floss support head comprises four of said fingers and wherein said closed loop of dental floss is supported in two pairs of spaced parallel lengths with the lengths of floss of the two pairs being substantially perpendicular to one another.

10. The dental flossing instrument according to claim 7 wherein said handle and said floss support head are formed as separate units and wherein said floss support head is releasably mounted on said one end of said handle.

* * * * *